United States Patent [19]

Zenitani et al.

[11] Patent Number: 4,494,539
[45] Date of Patent: Jan. 22, 1985

[54] METHOD AND APPARATUS FOR SURGICAL OPERATION USING MICROWAVES

[76] Inventors: Toshio Zenitani, 1-23-603, Nigawa-kita 1-chome, Takarazuka-shi, Hyogo-ken, Japan, 665; Katsuyoshi Tabuse, 831-54, Otani, Wakayama-shi, Wakayama-ken, Japan, 640

[21] Appl. No.: 374,884

[22] Filed: May 4, 1982

[30] Foreign Application Priority Data

Apr. 3, 1982 [JP] Japan .................................. 57-55583
Apr. 3, 1982 [JP] Japan .................................. 57-55584

[51] Int. Cl.$^3$ .............................................. A61B 17/36
[52] U.S. Cl. ........................... 128/303.1; 128/303.15; 128/303.17
[58] Field of Search ........... 128/303.1, 303.13–303.18, 128/804

[56] References Cited

U.S. PATENT DOCUMENTS 4,204,549 5/1980 Paglione ......................... 128/804 X
4,409,993 10/1983 Furihata ........................... 128/303.1

FOREIGN PATENT DOCUMENTS 0048402 3/1982 European Pat. Off. ........ 128/303.15
1143937 2/1963 Fed. Rep. of Germany ...... 128/804
1145279 3/1963 Fed. Rep. of Germany ...... 128/804

*Primary Examiner*—Lee S. Cohen
*Attorney, Agent, or Firm*—Darby & Darby

[57] ABSTRACT

The present application discloses an invention of a surgical operation method using microwave characterized in that microwaves are radiated to bio-tissue from a monopolar type operating electrode attached to the tip of a coaxial cable for transmitting microwaves, and an operation of coagulation, hemostasis or transection is performed on the bio-tissue with the use of thermal energy generated from the reaction of the microwaves on the bio-tissue. The bio-tissue can be operated in an easy, safe and bloodless manner. Therefore, the present method can be utilized for an operation on a parenchymatous organ having a great blood content or for coagulation or transection on a parenchymatous tumor.

According to the present method, there can be performed an operation on liver cancer which has been conventionally regarded as very difficult.

Apparatus for embodying the present method can be economically manufactured in a small size.

3 Claims, 4 Drawing Figures

METHOD AND APPARATUS FOR SURGICAL OPERATION USING MICROWAVES

FIELD OF THE ART

The present invention relates to a surgical operation method using microwave according to which an operation of coagulation, hemostasis or transection is performed on bio-tissue with the use of thermal energy generated from the reaction of microwaves on the bio-tissue and an operation, for example, on a parenchymatous organ having a great blood content can be performed in an easy, safe and bloodless manner.

BACKGROUND OF THE INVENTION

As an operation device, there are conventionally known an electrocautery (high frequency knife) and a laser operation device (laser knife).

The electrocautery uses a power supply with frequency of 0.3 to 10 MHz, wavelength of 1000 to 30 m and output of 200 to 500 W, and includes a high frequency operating electrode of the knife or tweezers type and a nonactive electrode.

With the nonactive electrode mounted to the other part of patient body, a high frequency current is flowed from the operating electrode to the nonactive electrode, so that hemostasis or coagulation is performed by cauterizing the tissue with the use of high frequency spark discharge. Accordingly, there is the danger of the patient often getting burnt. Moreover, the tissue is carbonizingly degenerated and thus carbonizingly degenerated tissue comes off with the passage of time, thereby to cause rehemorrhage which is very dangerous. Therefore, such electrocautery is not suitable to an operation on a parenchymatous organ having a great blood content.

Moreover, on the clinical practice, there is the danger of the patient being injured or receiving an electric shock. There are also pointed out that, at the stump, secondary hemorrhage after operation and cholerrhagia after operation are observed.

On the other hand, the laser operation device uses a power supply with wavelength of 10.6 μm and output of 50 to 100 W, and includes a hand piece of the condensing lense type. Therefore, upon each operation, the focus of the laser beams should be adjusted. If the radiation period of time is improperly set, such laser beams become too strong. Accordingly, there is the danger of other tissue being easily broken.

Moreover, if there is a slight error in setting the angle of the arm for transmitting the laser beams, the optical axis is erroneously set and the beams are subsequently radiated in unexpected directions. It is further to be pointed out that the arm moving range is limited to a predetermined range in view of the laser optical axis.

Since, for performing hemostasis or coagulation, the laser operation device utilizes thermal energy generated from the laser beams, the tissue is not carbonizingly degenerated. However, the maximal diameter of the vessels which are possibly made the hemostasis, is as small as 1.5 mm. Therefore, when the blood vessels have diameters of 1.5 mm or more, it is disadvantageously required to ligate such vessels before amputating them. Accordingly, the laser operation device is not suitable for an emergency operation.

Moreover, the maximal diameter of the intrahepatic bile duct which is possibly made the coagulation closing, is as small as 1.0 mm.

After the operation has been performed with such laser device, the serum GOT, GPT and Al-p are suddenly reduced after the third day and are recovered as late as after one week.

Such laser operation device of this type is of large size and very expensive.

SUMMARY OF THE INVENTION

It is an object of the present invention to provide a surgical operation method using microwave in which microwaves are radiated to bio-tissue from a monopolar type operating electrode disposed at the tip of a coaxial cable for transmitting microwaves, and an operation of coagulation, hemostasis or transection is performed on the bio-tissue with the use of thermal energy generated from the reaction of the microwaves on the bio-tissue.

BRIEF DESCRIPTION OF THE DRAWINGS

The present invention will be further discussed, by way of example, with reference to the accompanying drawings, in which.

DETAILED DESCRIPTION OF THE PREFERRED EMBODIMENTS

The description hereinafter will be made, in detail, of the first embodiment of the present invention with reference to FIG. 1.

Figure 1:
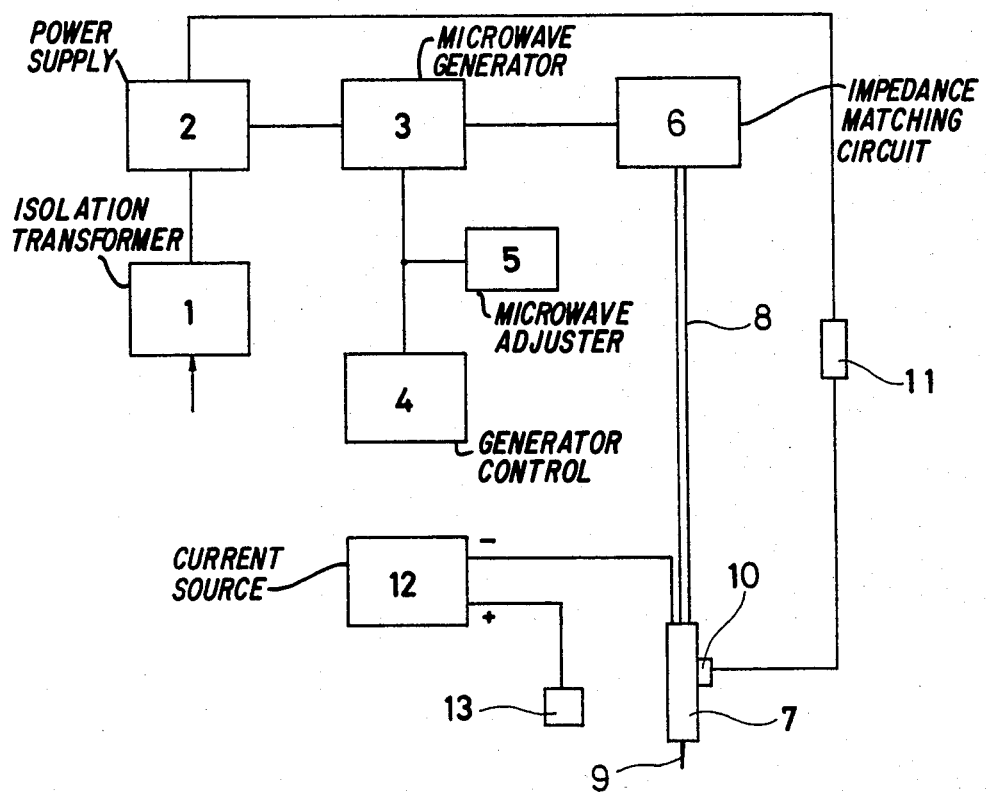
FIG. 1 is a block diagram of a first embodiment of surgical operation method using microwave in accordance with the present invention.

In FIG. 1, a safety device 1 mainly uses a reinforced insulating transformer. A power supply 2 connected to the safety device 1 includes an automatic voltage stabilizer. A microwave generator device 3 connected to the power supply 2 is designed to give out a microwave of 2450 MHz with the maximum output 150 W. A device for selectively limiting the output time dependent on disease 4 is designed to set the microwave output and radiation time to be determined dependent on the diseased organ, the state of disease, the dimension and condition of the tissue, the part of operation, coagulation, hemostasis and transection, etc. Namely, the device 4 is disposed for limiting and controlling the output and oscillation time (normally within 60 seconds) of the microwave generator device 3, thereby to prevent an erroneous operation due to excessive radiation, thus enabling the operation using microwaves to be performed in a safe and secure manner.

There is disposed a microwave output fine adjuster device 5 for finely adjusting the output of the microwave generator device 3. A microwave output impedance matching device 6 is connected to the microwave generator device 3. An operating hand piece 7 is connected to the impedance matching device 6 by a coaxial cable 8. A monopolar type operating electrode 9 in the needle form has a diameter of 0.5 mm and a length of 3.9 to 31.5 mm, and is attached to the hand piece 7. A hand switch 10 attached to the hand piece 7 is adapted to be turned ON when strongly grasped, and to be turned OFF when the grasping is loosened. A normally closed-type safety foot switch 11 is connected in series to the hand switch 10 and the primary side of the high voltage transformer in the power supply 2. This foot switch 11 is adapted to be turned OFF if pressed by the operator foot in the case of emergency.

An indifferent electrode 13 is connected to the positive terminal of an electric source of the tissue dissociation 12 and is adapted to come in contact with tissue adjacent the part of operation. The negative terminal of the electric source 12 is connected to the operating electrode of the hand piece 7.

The safety device 1 is disposed to prevent a high voltage applied to the microwave generator device 3 or a high frequency current therefrom, from electrically injuring the operator and the patient under operation.

The power supply 2 is a rectified power supply for actuating the microwave generator 3 in a stable manner, and can restrain sudden variations of the microwave output caused by variations of the input commercial AC power supply, during the operation is being performed.

The description hereinafter will discuss how the first embodiment of the present invention is operated.

The operating electrode 9 of the hand piece 7 is inserted into or contacted with the bio-tissue to be operated. The hand switch 10 of the hand piece 7 is turned ON. Microwaves generated by the microwave generator device 3 are then transmitted to the operating electrode 9 through the microwave output impedance matching device 6 and the coaxial cable 8. The microwaves are radiated from the operating electrode 9 to the inside or the surface of the tissue to be operated.

At this time, the bio-tissue is dielectrically heated by thermal energy generated from the reaction of the radiated microwaves on the bio-tissue, whereby an operation of transection coagulation or hemostasis is performed on the tissue.

By turning ON or OFF the hand switch 10 of the hand piece 7, the radiation of microwaves is started or stopped, respectively. When the hand switch 10 or the foot switch 11 is turned OFF, the high voltage is shut off to stop the radiation of microwaves.

In actually performing an operation using microwaves, the microwave output and the microwave applying period of time are selected taking the tissue condition and the vessel sizes, etc. into account, based on the conditions shown in the following table:

| Organ | Microwave output (W) | Applying time (second) |
| --- | --- | --- |
| Liver | 30–60 | 30–60 |
| Spleen | 30–60 | 30–60 |
| Ovary | 20–50 | 20–30 |
| Parenchymatous tumor | 50 | 30–60 |

It is to be noted that microwave energy is concentrated on the tissue under operation, and therefore exerts no influence upon the tissue 15 mm or more apart from the shaft center of the operating electrode 9. Moreover, since the present invention does not require a nonactive electrode, no microwave current flows in the other part of the patient body, so that no other tissue is injured.

When the operating electrode 9 is pulled out after the completion of an operation using microwaves made with the operating electrode 9 inserted into the bio-tissue, moisture in the tissue around the operating electrode 9 is evaporated by dielectric heat of the microwaves and the coagulated tissue disadvantageously sticks to the operating electrode 9. In the embodiment of the invention, however, after the completion of the operation, a cathodal direct current (abt. 10–15 mA) is flowed for a very short period of time (abt. 5 seconds) from the electric source for the tissue dissociation 12 to the operating electrode 9. Moisture is accordingly generated on the interface between the bio-tissue and the operating electrode 9 by eletrolysis. Therefore, the tissue coagulated by dielectric heating of the microwaves, does not stick to the operating electrode 9, thereby to facilitate the dissociation of the operating electrode 9 from the bio-tissue.

The description hereinafter will discuss the second embodiment of the surgical operation method using microwave in accordance with the present invention, with reference to FIG. 2.

Figure 2:
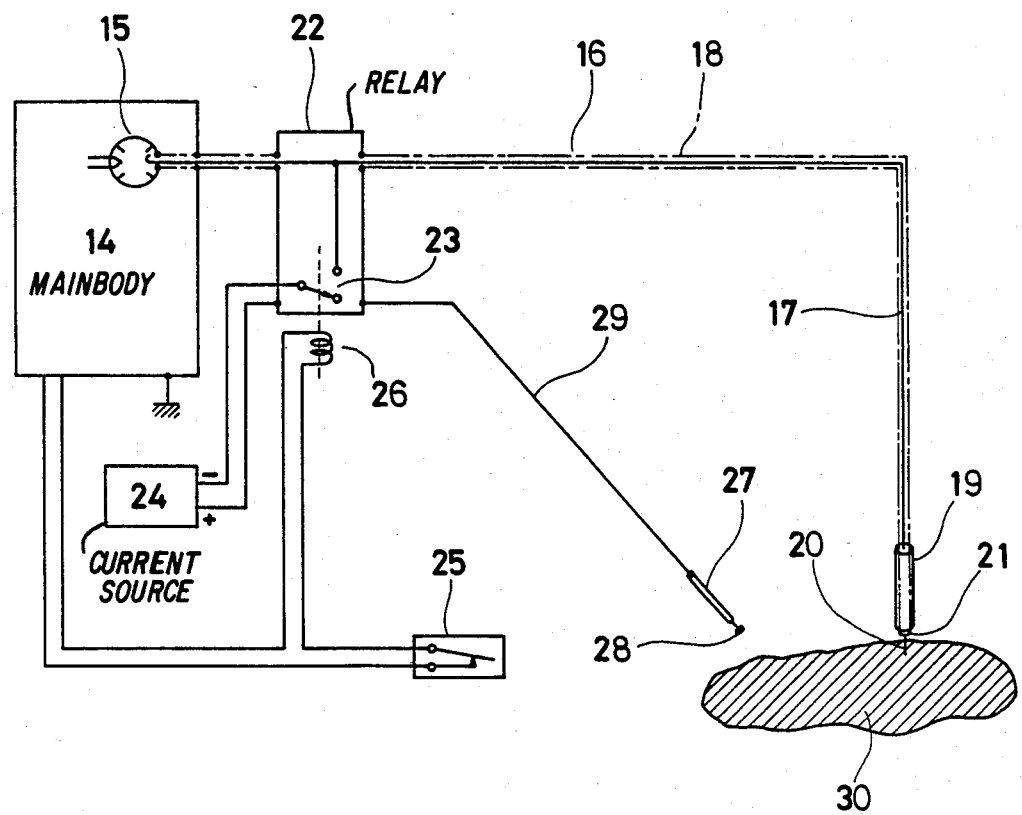
FIG. 2 is a schematic view of a second embodiment of surgical operation method using microwave in accordance with the present invention.

In FIG. 2, a microwave operation device main body 14 incorporates a magnetron 15. A coaxial cable 16 comprises a core wire 17 and a shield conductor 18. A monopolar type operating electrode 20 in the needle shape is attached to the tip of an operating hand piece 19. This operating electrode 20 is connected to the output intake loop of the magnetron 15 through the core wire 17. A shield metal member 21 disposed outside the base portion of the operating electrode 20 is connected to the shield conductor 18 of the coaxial cable 16. The shield conductor 18 is connected to the positive electrode of the magnetron 15 and is grounded in the operating device main body 14.

A coaxial relay device 22 incorporates a relay switch 23, of which one contact is connected to the core wire 17 of the coaxial cable 16. An electric source for the tissue dissociation 24 has a negative terminal connected to the changeover terminal of the relay switch 23 and a positive terminal connected to the shield conductor 18 of the coaxial cable 16 through the coaxial relay 22. A normally closed-type foot switch 25 is connected to the operation device main body 14. A relay coil 26 for actuating the relay switch 23 is connected in series to the foot switch 25 and the operation device main body 14. During the foot switch 25 is not being actuated, a high voltage is supplied from the power supply of the operation device main body 14 to the magnetron 15 and the relay coil 25 is excited to connect the relay switch 23 to the open contact.

When the foot switch 25 is pressed by the operator foot to be turned OFF, current supply to the magnetron 15 in the operation device main body 14 is stopped and no current flows to the relay coil 26. The relay switch 23 is then switched and the negative terminal of the electric source for the tissue dissociation 24 is connected to the core wire 17.

A hand piece for positive electrode 27 has at the tip thereof a positive electrode 28 to which a lead wire 29 is connected. The lead wire 29 is also connected to the positive terminal of the electric source 24 through the coaxial relay 22. To dissociate the operating electrode 20 from the coagulated bio-tissue, the positive electrode 28 is adapted to come in contact with the bio-tissue adjacent the part of operation.

The bio-tissue, in particular the diseased tissue, of a parenchymatous organ is generally designated by numeral 30.

The description hereinafter will discuss how the second embodiment of the present invention is operated.

The operating electrode 20 of the hand piece 19 is inserted into the part of lesion in the bio-tissue 30. When the operation device main body 14 is driven, microwaves generated by the magnetron 15 are transmitted to the operating electrode 20 through the core wire 17 and radiated to the part of lesion for 30 to 60 seconds. With the use of dielectric heat produced at this time, hemostasis, coagulation or partial transection is performed on the bio-tissue 30.

After the operation using microwaves has been finished, the foot switch 25 is turned OFF so that the supply of microwaves is stopped and the relay switch 23 of the coaxial relay device 22 is switched. Then, the negative terminal of the electric source for the tissue dissociation 24 is connected to the operating electrode 20 through the core wire 17. When either the positive electrode 28 of the hand piece for positive electrode 27 is contacted with the bio-tissue 30, or the shield metal member 21 disposed at the tip of the operating hand piece 19 is pressingly contacted with the bio-tissue 30, a cathodal direct current of about 10 mA is flowed from the electric source 24 to the operating electrode 20 for a very short period of time (Abt. 5 seconds). Moisture is then produced on the interface between the operating electrode 20 and the bio-tissue 30 by electrolysis, and electroosmosis thereby to facilitate the dissociation of the operating electrode 20 from the bio-tissue 30. Dependent on the condition of the bio-tissue 30, the part of operation, the operation method and other, it may be suitably judged how such dissociation is performed, either by the contact of the positive electrode 28 with the bio-tissue 30 or the contact of the shield metal member 21 with the bio-tissue 30.

The description hereinafter will discuss the third embodiment of the operation method using microwave in accordance with the present invention, with reference to FIGS. 3 and 4.

In the third embodiment, the present invention is applied to an operation to be performed on the organs in vivo with the use of a medical endoscope.

Figure 3:
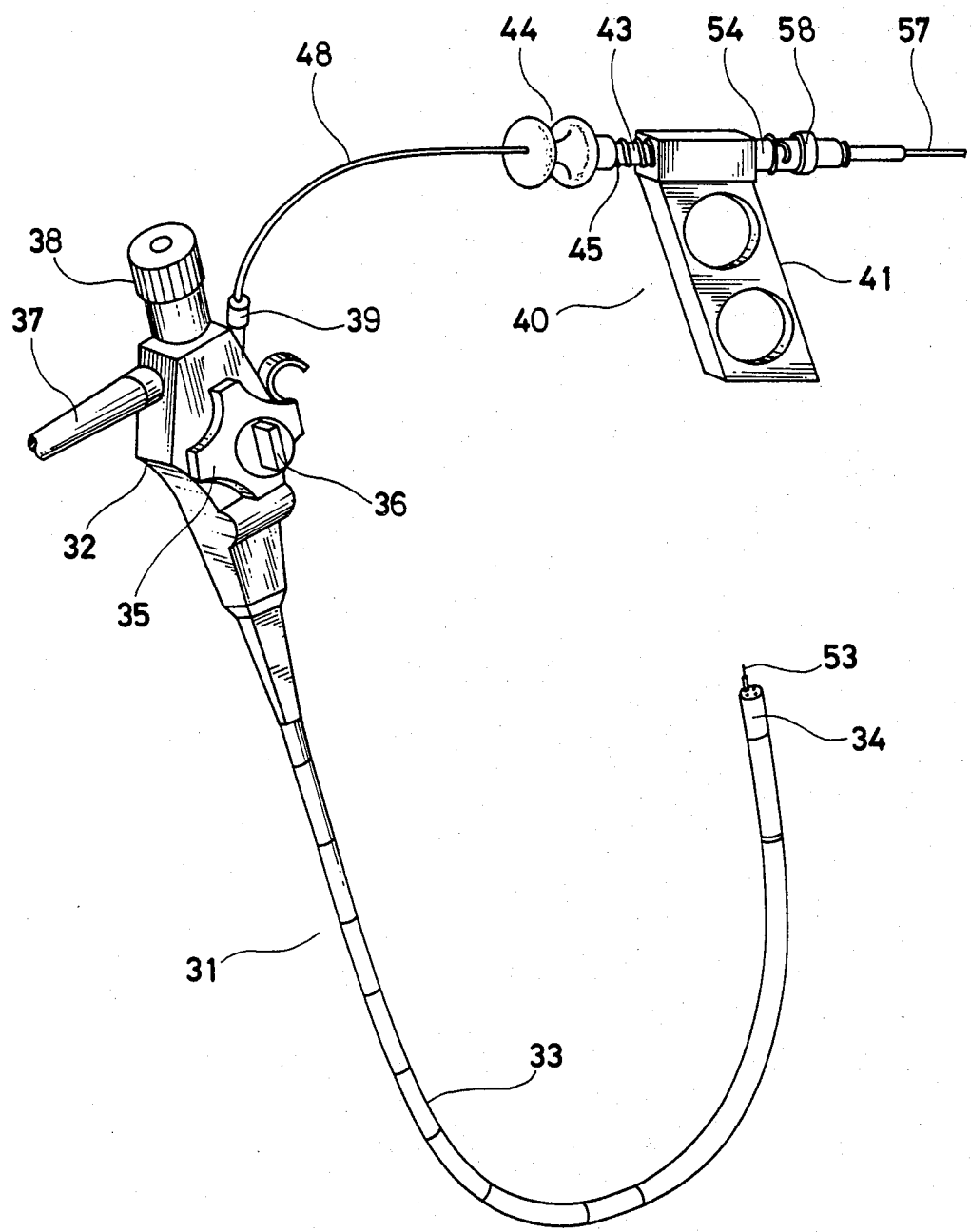
FIG. 3 is a perspective view of main portions of a third embodiment of surgical operation method using microwave in accordance with the present invention.
Figure 4:
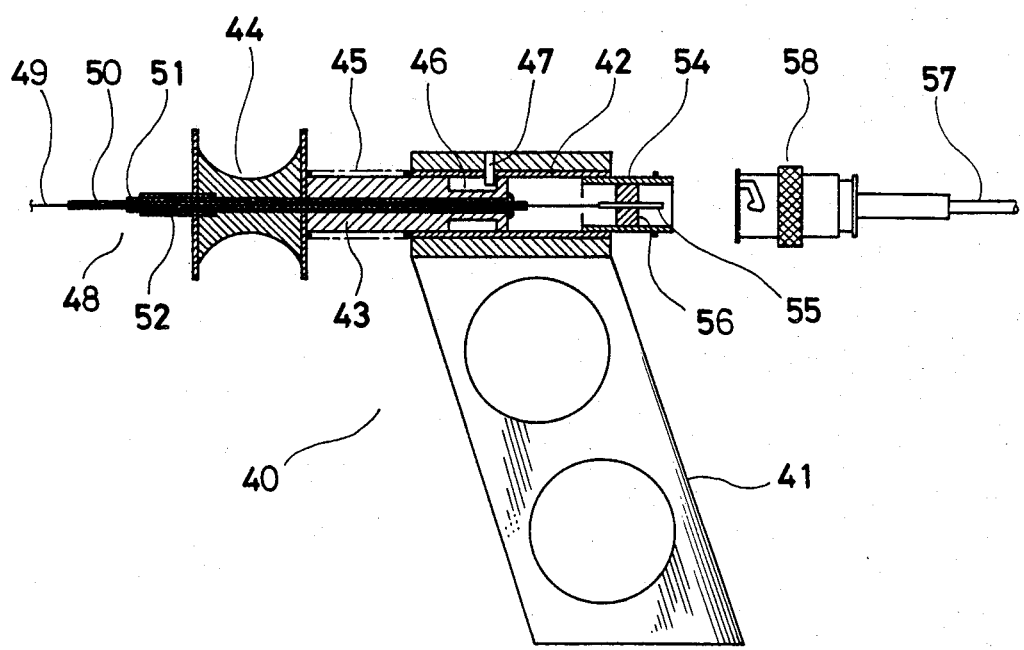
FIG. 4 is a section view of the manipulating unit in FIG. 3.

In FIGS. 3 and 4, with the use of a medical endoscope 31 of the conventionally known type, the inside of the organs in vivo, in particular the stomach, can be directly observed from the outside of the living body, so that clinical diagnosis is made in a very easy and secure manner.

The medical endoscope 31 has a manipulating portion 32 and a detector portion 34 which is integrally constructed with the manipulating portion 32 through a portion to be inserted in vivo 33. The detector portion 34 is provided in the end surface thereof with a projection light guide hole, an observation image guide hole, an air and water feed hole, a forceps hole and other.

The manipulating portion 32 has angle knobs 35 and 36 for variously adjusting the detector portion 34 vertically and horizontally.

The medical endoscope 34 has a light guide 37 and an eye contact portion 38. A forceps channel 39 communicates with the forceps hole in the detector portion 34. For example, a slender forceps may be inserted into the forceps channel 39 and the tip of the forceps is projected from the forceps hole such that the organ and tissue in vivo can be held or pressed by external manipulation.

A manipulating unit 40 for operation using microwaves has a hand grip 41. A cylindrical holding member 42 passes through the head of the hand grip 41. A slidable member 43 is slidably fitted to one side of the cylindrical holding member 42. A finger holding portion 44 in the substantially hand drum shape is disposed at the tip of the slidable member 43 in a unitary construction therewith. The slidable member 43 may be slided by operating the finger holding portion 44 with the finger of the hand which grips the hand grip 41.

A reset coil spring 45 is disposed outside the slidable member 43 between the hand grip 41 and the finger holding portion 44. An engagement groove 46 is formed in the outer circumference of the slidable member 43 at the base side thereof.

A pin 47 is inserted into the head of the hand grip 41, and has a tip which engages with the engagement groove 46 in the slidable member 43, thereby to prevent the coil spring 45 from coming out from the slidable member 43.

A coaxial cable for transmitting microwaves 48 is extended from the manipulating unit 40, and comprises a center conductor 49, an inner insulating member 50, an outer conductor 51 and an outer shield 52, these members 49, 50, 51 and 52 being concentrically disposed. The respective base ends of the center conductor 49, the inner insulating member 50 and the outer conductor 51 of the coaxial cable 48 are introduced in the cylindrical holding member 42 after passing through the finger holding portion 44 and the slidable member 43. The end of the outer conductor 51 engages with the end surface of the base portion of the slidable member 43. The center conductor 49 is slidable with respect to the inner insulating member 50. The tip portion of the coaxial cable 48 is inserted into the forceps channel 39 of the medical endoscope 31 and is projected from the forceps hole of the detector unit 34 through the inserting portion 33.

A monopolar type operating electrode 53 adapted to be projected and housed is constructed integrally with the center conductor 49 of the coaxial cable 48 projecting from the forceps hole.

A manipulation-side coaxial connector 54 is fitted to the other side of the holding member 42 of the hand grip 41 and is provided at the center of the inside thereof with a center electrode for connection 55 which is held by a holding member 56. This center electrode 55 is connected to the center conductor 49 of the coaxial cable 48 in the straight line form.

A coaxial cable for transmitting microwaves 57 is connected to a microwave operation device (not shown) having a power supply, a microwave generator device and other. A current-supply-side coaxial connector 58 is disposed at the tip of the coaxial cable 57 and connected to the manipulation-side coaxial connector 54. The coaxial connector 58 incorporates an electrode to be connected and disconnected to the center electrode 55 of the manipulation-side coaxial connector 54.

The description hereinafter will discuss how the third embodiment of the present invention is operated.

The detector portion 34 and the inserting portion 33 of the medical endoscope 31 are inserted in vivo. While controlling the angle knobs 35 and 36 of the manipulating portion 32, the detector portion 34 is guided to the part of lesion in the organ in vivo, for example in the stomach. With the hand grip 41 grasped with one hand, the finger holding portion 44 is pulled, with the finger, toward the operator against the spring-load of the coil spring 45. Then, the finger holding portion 44 and the slidable member 43 are slid into the cylindrical holding member 42. The outer conductor 51 of the coaxial cable 48 of which the end is engaged with the slidable member 43, is moved toward the operator, i.e. toward the center electrode 55, according to the movement of the slidable member 43. The inner insulating member 50 of the coaxial cable 48 is integral with the outer conductor 51, and the inner conductor 49 is slidable with respect to the inner insulating member 50. Therefore, according to the movement of the outer conductor 51, the inner insulating member 50 is slided toward the center conductor 49, and the operating electrode 53 integral with the center conductor 49 is projected from the tip of the detector portion 34 of the endoscope 31. Thus projected operating electrode 53 is contacted with or inserted into the diseased tissue. When the microwave operation device is then driven, microwaves generated by the microwave generator device are transmitted to the operating electrode 53 through the coaxial cables 57 and 48.

The microwaves are radiated from the operating electrode 53 to the diseased tissue. Thus, an operation of hemostasis or coagulation is performed on the diseased tissue with the use of thermal energy generated from the reaction of the microwaves with the bio-tissue. After the operation has been completed, the pulling of the finger holding portion 44 of the manipulating unit 40 is released. By the spring-load of the coil spring 45, the slidable member 43 is then slid together with the finger holding portion 44 in the direction opposite to that above-mentioned. Thus, the operating electrode 53 at the tip of the medical endoscope 31 is housed. It is to be noted that such procedures can be all performed under the direct observation by the operator through the eye contact portion 38 of the manipulating portion 32.

INDUSTRIAL UTILITY

According to the surgical operation method using microwave of the present invention, an operation of coagulation, hemostasis or transection may be performed on bio-tissue with the use of thermal energy generated from the reaction of microwaves on the bio-tissue. The bio-tissue may be operated in an easy, safe and bloodless manner. Therefore, the present method can be utilized for an operation on a parenchymatous organ having a great blood content such as the brain, lungs, liver, spleen, kidney or ovary, and also for coagulation or transection (partial transection) of a parenchymatous tumor. Therefore, when hemostasis or partial transection is made according to the present method, the spleen can be preserved. Thus, there can be expected a wide applicability of the present method to an operation which has been conventionally regarded as very difficult.

Apparatus for embodying the surgical operation method using microwave in accordance with the present invention, uses a power supply, for example, with frequency of 2450 MHz, wavelength of 12 cm and output of 30-100 W, and does not require a nonactive electrode as done in an electrocautery, so that such apparatus can be economically manufactured in a small size and its manipulation is very easy.

The advantages to be obtained with the use of the surgical operation method using microwave in accordance with the present invention, will be discussed in the following.

The maximal diameters of the vessels which are possibly made the hemostasis, can be widened to as large as 3 mm for the artery and the vein, and the maximal diameter of the introhepatic bile duct which is possibly made the coagulation closing, can be also widened to as large as 3 mm. At the liver stump, there is observed neither secondary hemorrhage after operation nor cholerrhagia after operation.

The remnant period of the coagulation necrosis tissue is as long as 3 to 6 months, so that hemostasis can be securely performed.

By the action of microwave heat generated in the bio-tissue, many kinds of bacteria are sterilized and no blood stream is present, so that no infection takes place.

The decrement rate of stretch moment of the coagulated vessels is 18.6% for the artery and 17.5% for the vein. The regeneration rate of remnant liver cell (the weight of liver) is 140% on the 21th day after the operation of 30% partial transection on the liver.

As to the general effects for the body condition, the bodily temperature does not rise and no irreversible change followed by the break of tissue is observed. The conditions of the serum GOT, GPT and Al-p get recovery 24 hours after the operation. There is no risk of hepatopathy occurring thereafter.

Observation 6 months after the operation does not show any complicating diseases and general effects for the body condition peculiar in the present method.

After the completion of the operation using microwave according to the present invention, a cathodal current is supplied to the operating electrode inserted in the bio-tissue, thus enabling the operating electrode to be dissociated. Therefore, no coagulated tissue is sticked to the operating electrode at the time of dissociation, thus eliminating the necessity of pulling the operating electrode with the use of some instrument such as TZUPEL. Accordingly, the operation can be more smoothly performed.

When the present invention is applied to a medical endoscope, an operating electrode attached to the tip of a coaxial cable is projected from the tip of the inserting portion of the medical endoscope. Therefore, the diseased tissue in the organ in vivo can be operated with the use of microwaves outside the living body.

Furthermore, since the operation can be performed under the direct observation, such operation can be safely and accurately conducted on, for example, gastric ulcer or gastric cancer.

What we claim is:

1. A surgical operation method utilizing microwave energy comprising the steps of:
   inserting a monopolar type operating electrode into bio-tissue;
   radiating microwave energy from said operating electrode into said bio-tissue for performing coagulation, hemostasis, or transection on said bio-tissue with thermal energy generated from the reaction of said microwaves on said bio-tissue; and
   applying a predetermined cathodal current for a predetermined period to said operating electrode after completion of said radiation of microwave energy, thereby generating moisture by electrolysis on an interface between said operating electrode and said bio-tissue to enable said operating electrode to be dissociated from said bio-tissue.

2. The surgical method according to claim 1 wherein said operating electrode is coupled to a coaxial cable which is in turn coupled to a source of microwave energy for generating said radiated microwave energy further comprising the steps of:

inserting said coaxial cable into a medical endoscope having a tip portion such that said operating electrode projects from said tip portion; and inserting said operating electrode in vivo with said endoscope, whereby said operation is performed on said bio-tissue under direct observation.

3. A surgical operation device comprising:

microwave generator means, having an output terminal, for generating microwaves at said output terminal;

microwave output impedance matching means having a coaxial cable electrically coupled to said generator means output terminal; a needle-form monopolar operating electrode electrically coupled to said coaxial cable; and means for tissue dissociation including an electric source having a positive terminal electrically coupled to a positive electrode adapted to come in contact with tissue adjacent to the part of operation, and a negative terminal electrically coupled to said operating electrode for dissociating said operating electrode from coagulated tissue.

* * * * *